(12) United States Patent
Giambattista et al.

(10) Patent No.: US 6,248,095 B1
(45) Date of Patent: Jun. 19, 2001

(54) LOW-COST MEDICATION DELIVERY PEN

(75) Inventors: Lucio Giambattista, East Hanover, NJ (US); Carlos Guillermo, East Hampton; John Burbank, Ridgefield, both of CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/027,607

(22) Filed: Feb. 23, 1998

(51) Int. Cl.[7] ........................................ A61M 5/00
(52) U.S. Cl. ................................................ 604/207
(58) Field of Search .............................. 604/207, 208, 604/209, 210, 211, 187, 218, 224; 222/32, 637

(56) References Cited

U.S. PATENT DOCUMENTS

| | | | |
|---|---|---|---|
| 4,936,833 | * | 6/1990 | Sams ................................... 604/232 |
| 5,304,152 | * | 4/1994 | Sams . |
| 5,308,340 | * | 5/1994 | Harris .................................. 604/208 |
| 5,383,865 | * | 1/1995 | Michel . |
| 5,514,097 | * | 5/1996 | Knauer . |
| 5,584,815 | * | 12/1996 | Pawelka et al. . |

\* cited by examiner

*Primary Examiner*—Sharon Kennedy
*Assistant Examiner*—Catherine Serke
(74) *Attorney, Agent, or Firm*—Alan W. Fiedler

(57) ABSTRACT

A medication delivery pen having very few parts allowing it to be manufactured at a very low-cost. The medication delivery pen also includes an automatic release mechanism to allow the user to easily reset the dose on the medication delivery pen and a mechanism for allowing the lead screw to easily retract back into the body of the medication delivery pen when the vial retainer has been removed to receive a new vial.

7 Claims, 4 Drawing Sheets

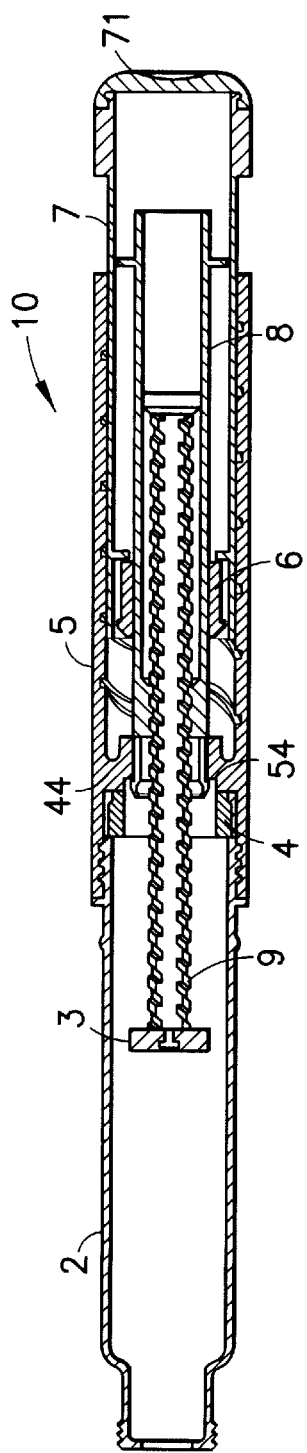
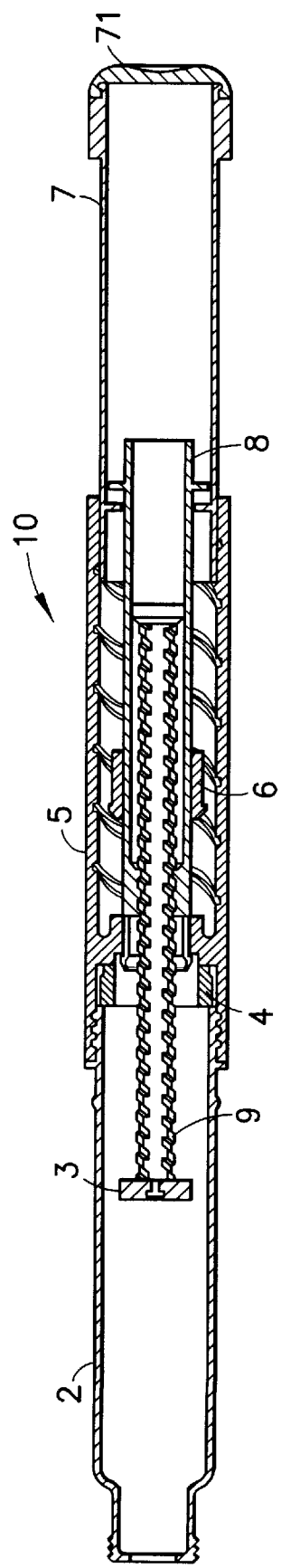

LOW-COST MEDICATION DELIVERY PEN

BACKGROUND OF THE INVENTION

1. Field of the Invention

The present invention relates to a medication delivery pen having a variety of features and, more particularly, a low-cost medication delivery pen having very few parts.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described medication delivery pen is effective and much more convenient for self-administration of medication than the hypodermic syringes that use separate medication vials. However, the above-described medication delivery pen requires a number of parts which make the manufacture of these pens very expensive. Hence, it is necessary to provide a medication delivery pen having a simple mechanism for setting the desired dose that uses as few parts as necessary without losing functionality or standard features.

SUMMARY OF THE INVENTION

The present invention relates to a medication delivery pen that addresses the aboveidentified problems. The medication delivery pen uses only tens parts and still provides numerous features that have become expected by medical delivery pen users.

The medication delivery pen according to the present invention includes a mechanism that automatically disengages the drive mechanism from the dose control mechanism to permit the user to reset the dose on the medication delivery pen.

Another feature of the present invention is an automatic mechanism that allows the user to easily load a new vial and reposition the lead screw when the vial retainer has been removed from the body of the medication delivery pen.

BRIEF DESCRIPTION OF THE DRAWINGS

FIG. 9 is a cross-sectional view of the medication delivery pen shown in FIG. 1 fully assembled and in a dose setting condition.

FIG. 10 is a cross-sectional view of the medication delivery pen shown in FIG. 9 in a reset dose condition.

DETAILED DESCRIPTION OF THE INVENTION

Figure 1:
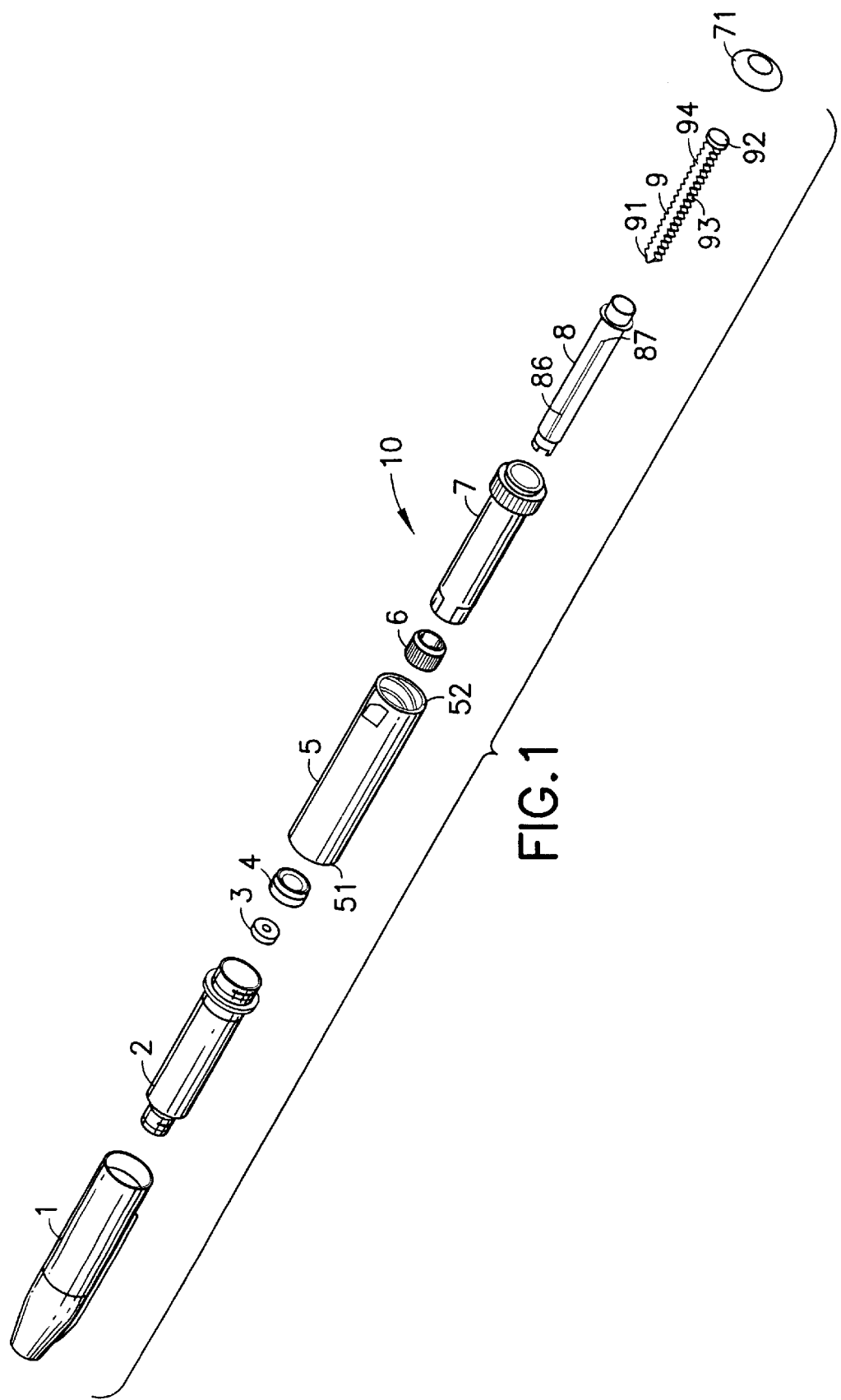
FIG. 1 is an exploded perspective view of a medication delivery pen according to the present invention.

A medication delivery pen 10 according to the present invention is shown in FIG. 1. Medication delivery pen 10 includes a cap 1 removably attached to a vial retainer 2 so to cover vial retainer 2 between uses of medication delivery pen 10. Vial retainer 2 receives a vial (not shown) that is commonly used in such medication delivery pens to provide medication and/or insulin for an injection. Medication delivery pen 10 includes a body 5 having a distal end 51 and a proximal end 52, with vial retainer 2 being attached to distal end 51 of body 5. Medication delivery pen 10 also includes a dose set knob 7, a driver 8, a lead screw 9, a lead screw spinner 3, a retract nut 4, a reset ring 6, and a thumb button 71. Each of these elements are more clearly shown in FIGS. 2–8 and are more fully described below.

Figure 2:
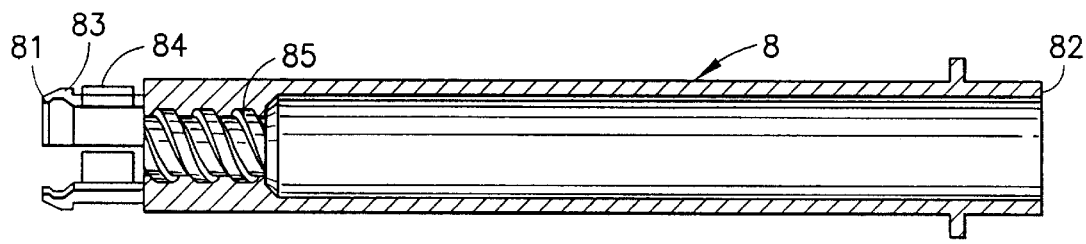
FIG. 2 is a cross-sectional view of the driver in the medication delivery pen shown in FIG. 1.
Figure 3:
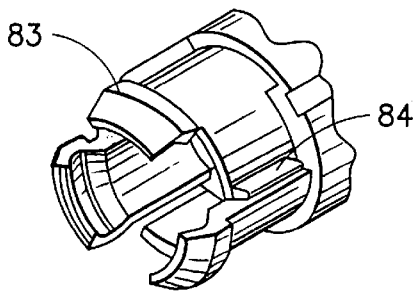
FIG. 3 is a partial perspective view of the distal end of the driver shown in FIG. 2.

FIG. 2 is a cross-sectional view of driver 8 having a distal end 81 and a proximal end 82, wherein distal end 81 includes a snap ring 83 used to attach retract nut 4 onto distal end 81 of driver 8. In addition, driver 8 includes a plurality of ratchet fingers 84 at distal end 81, as more clearly shown in FIG. 3. These ratchet fingers 84 engage a ratchet 53, shown in FIG. 6, within body 5 to allow driver 8 to rotate only in one direction with respect to body 5. Driver 8 also includes a set of threads 85 that interface with a matching set of threads 93 on lead screw 9, shown in FIG. 1.

Figure 4:
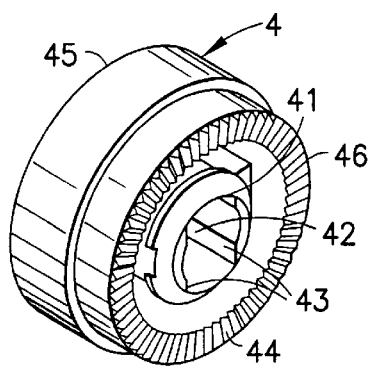
FIG. 4 is a perspective view of the retract nut shown in FIG. 1.

FIG. 4 is a perspective view of retract nut 4 that more clearly shows an attachment ring 41 that mates with snap ring 83 on distal end 81 of driver 8 to rotatably attach retract nut 4 onto driver 8. Retract nut 4 also includes an opening 42 therethrough having a pair of flat sides 43 that mate with set of flat sides 94 on lead screw 9, shown in FIG. 1, to prevent lead screw 9 from rotating with respect to retract nut 4. Retract nut 4 also has a distal surface 45 and a proximal end 46, proximal end 46 having a set of radial splines 44 that mates with a set of radial splines 54 within body 5 to prevent retract nut 4 and lead screw 9 from rotating when these splines 44 and 54 are engaged. As more clearly shown in FIG. 9, these splines 44 and 54 are fully engaged when vial retainer 2 is mounted onto body 5 and accordingly prevent retract nut 4 and lead screw 9 from rotating with respect to body 5. However, when vial retainer 2 is not mounted into body 5, retract nut 4 and lead screw 9 are free to rotate which permits lead screw 9 to be free to backdrive into body 5 as the user pushes a new vial into place. A lead screw spinner 3 is attached to a distal end 91 of lead screw 9 and is allowed to spin freely on lead screw 9, shown in FIG. 1, in relation to a rubber plunger (not shown) within the vial as lead screw 9 is backdriven into body 5.

When vial retainer 2 locks retract nut 4 into mating radial splines 54 within body 5, lead screw 9 is locked against rotation which then enables threads 85 within driver 8 to drive lead screw 9 in the distal direction towards and against the rubber plunger within the vial during a dispensing operation. Snap ring 83 on driver 8 also allows retract nut 4 to float captive thereon thus trapping it from spinning down lead screw 9, when exchanging vials should a user invert medication delivery pen 10 when changing vials.

Figure 5:
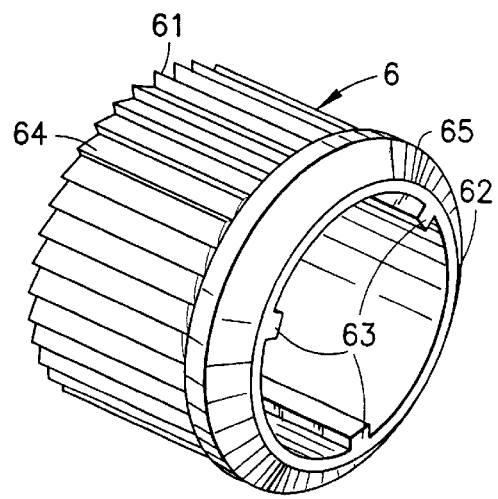
FIG. 5 is a perspective view of the reset ring shown in FIG. 1.

FIG. 5 is a perspective view of reset ring 6 having a plurality of keys 63 therein that travel within a respective set of keyways 86 on driver 8, shown in FIG. 1. Reset ring 6 also includes a distal end 61 and a proximal end 62, proximal end 62 having a flange 65 and a plurality of ratchets 64 extending from flange 65 to distal end 61. Ratchets 64 engage with a plurality of ratchet fingers 73 on a distal end 71 of dose set knob 7, shown in FIG. 8 and discussed further below.

Figure 6:
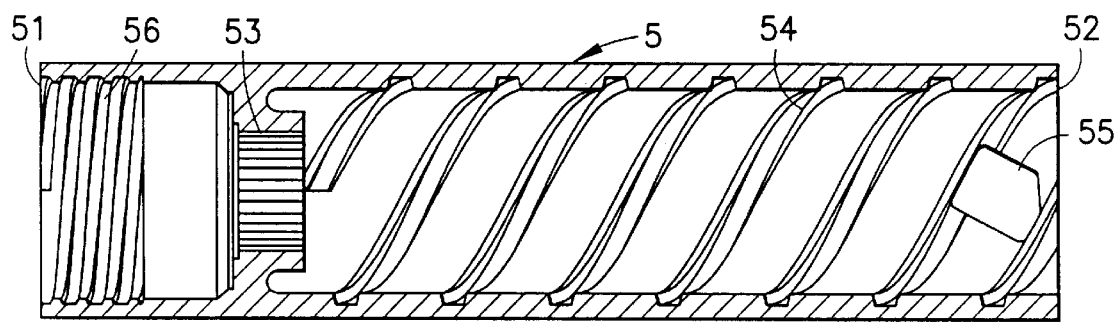
FIG. 6 is a cross-sectional view of the body of the medication delivery pen shown in FIG. 1.
Figure 7:
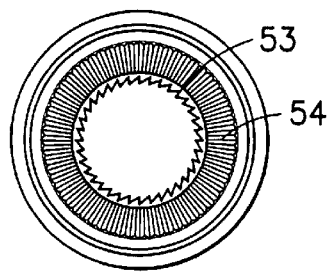
FIG. 7 is a distal end view of the body shown in FIG. 6.

FIG. 6 is a cross-sectional view of body 5 more clearly showing distal end 51 and proximal end 52 having a set of dose setting threads 58 therein together with a dose viewing window 55. Another set of threads 56 located within distal end 51 are used to attach vial retainer 2 in this embodiment. Of course, other means for attaching vial retainer 2 to body 5 could also be used and fall within the scope of the present invention as long as sufficient force is applied to retract nut 4 to prevent rotation of retract nut 4 and lead screw 9 within body 5 when vial retainer 2 is attached to body 5. FIG. 7 is a distal end view of body 5 more clearly showing radial splines 54.

Figure 8:
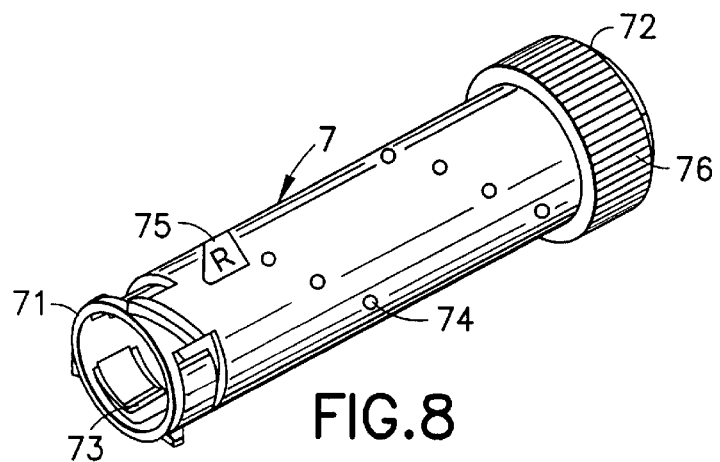
FIG. 8 is a perspective view of the dose set knob of the medication delivery pen shown in FIG. 1.

FIG. 8 is a perspective view of dose set knob 7 having a distal end 71 and a proximal end 72, with a textured section 76 near proximal end 72 to aide the user in turning dose set knob 7 to set a desired dose when using medication delivery pen 10. Distal end 71 includes the plurality of ratchet fingers 73 that engage ratchet 64 on reset ring 6 when setting a dose, as shown in FIG. 9, until medication delivery pen 10 is in a reset condition, as shown in FIG. 10. When medication delivery pen 10 is in the reset condition, reset ring 6 has disengaged from dose set knob 7 as clearly seen in FIG. 10. Alternatively, as shown in FIG. 9 during a dose setting condition, reset ring 6 is within dose set knob 7 such that ratchet 64 are engaged with ratchet fingers 73. When a user is turning dose set knob 7 and thereby turning reset ring 6 because of the engagement of ratchet 64 and ratchet fingers 73, keys 63 within reset ring 6 interact with keyways 86 on driver 8 to cause driver 8 to rotate about lead screw 9 and move driver 8 in a proximal direction along lead screw 9. After a desired dose has been set by the user using dose set knob 7 and the desired dose is to be dispensed, movement of dose set knob 7 in a distal direction will cause driver 8 to push lead screw 9 in the distal direction and thereby dispense medication from the vial.

The user sets a desired dose by rotating dose set knob 7 in a counter clockwise direction until the desired dose is displayed in dose display window 55 in body 5. Dose set knob 7 includes a plurality of dosage numerals 74 that show through window 55 and an "R" 75 that identifies a "reset condition" for medication delivery pen 10. When the desired dose is reached, the user depresses a thumb button 71 attached to proximal end 72 of dose set knob 7 until dose set knob 7 has fully returned within body 5.

A significant function of the drive mechanism within medication delivery pen 10 is that if the user overshoots the desired dose, medication delivery pen 10 can be reset so that the user may redial for the desired dose. This is accomplished by rotating dose set knob 7 completely past the maximum value (30 or 60) until an "R" on dose set knob 7 is displayed in window 55 within body 5. This disengages ratchet fingers 73 within dose set knob 7 from ratchet 64 on reset ring 6 by forcing them apart and releasing reset ring 6 from within dose set knob 7. This action is caused by keys 63 engaging with a set of stops 87, shown in FIG. 1, at a proximal end of each keyway 86 on driver 8. Dose set knob 7 is then free to rotate back to an initial dose position ("0") upon which ratchet fingers 73 are forced to reengage with ratchet 64 on reset ring 6. Disengaging and re-engaging ratchet 64 and ratchet fingers 73 requires significant tactile manipulation and results in an audible click which alerts the user that the resetting function has been performed.

While the present invention has been described with respect to a preferred embodiment, it is apparent that various changes can be made without departing from the scope of the invention as defined by the appended claims.

What is claimed is:

1. A medication delivery pen comprising:
   a body having a distal end and a proximal end and including:
   a dose control mechanism for setting a desired dose to be delivered and initiating a reset condition;
   a drive mechanism for dispensing the desired dose, said drive mechanism including a leadscrew having a set of threads and a driver having a set of threads that engage with the set of threads on said leadscrew to drive said leadscrew in a distal direction during dispensing; and
   a reset mechanism that is selectively activated by said dose control mechanism for disengaging said drive mechanism from said dose control mechanism when said dose control mechanism initiates the reset condition to permit a new desired dose to be set by said dose control mechanism without having to use said drive mechanism to dispense the previously set desired dose, said reset mechanism including an alert mechanism that alerts a user that the reset condition has been initiated,
   wherein said dose control mechanism includes a dose set knob rotatably mounted within said body and attached to said drive mechanism by said reset mechanism during a dose setting condition, and
   wherein said reset mechanism disengages said dose set knob from said driver when said dose set knob initiates the reset condition.

2. The medication delivery pen according to claim 1, wherein said body further includes a dose display window and said reset condition is defined by a "R" on said dose set knob that is displayed in said dose display window.

3. The medication delivery pen according to claim 1, wherein said reset mechanism includes a reset ring that travels on said driver and rotates said driver as said dose set knob is rotated during a dose setting condition.

4. The medication delivery pen according to claim 3, wherein said reset ring includes a ratchet that engages with a ratchet finger on said dose set knob to cause said reset ring to rotate with said dose set knob, wherein said ratchet finger and said ratchet are disengaged when said dose set knob is moved from the dose setting condition to a reset condition.

5. The medication delivery pen according to claim 4, wherein said reset ring further includes a key that engages with a keyway on said driver to rotate said driver as said dose set knob and said reset ring are rotated during the dose setting condition.

6. The medication delivery pen according to claim 1, further comprising:
   a vial retainer that mounts to said distal end of said body; and
   a reload mechanism that disengages said drive mechanism when said vial retainer is removed from said body to allow a user to reload said medication delivery pen.

7. The medication delivery pen according to claim 6, wherein said reload mechanism includes a retract nut in said body between said vial retainer and said drive mechanism that causes the drive mechanism to disengage when said vial retainer is removed from said body to allow a user to reload said medication delivery pen.

\* \* \* \* \*